US009314457B2

(12) United States Patent
Gibson et al.

(10) Patent No.: US 9,314,457 B2
(45) Date of Patent: Apr. 19, 2016

(54) METHODS OF TREATING AND PREVENTING VASCULAR INSTABILITY DISEASES

(71) Applicants: Christopher C. Gibson, Salt Lake City, UT (US); Dean Y. Li, Salt Lake City, UT (US)

(72) Inventors: Christopher C. Gibson, Salt Lake City, UT (US); Dean Y. Li, Salt Lake City, UT (US)

(73) Assignee: THE UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 0 days.

(21) Appl. No.: 14/728,800

(22) Filed: Jun. 2, 2015

(65) Prior Publication Data

US 2015/0366848 A1 Dec. 24, 2015

Related U.S. Application Data

(60) Provisional application No. 62/014,540, filed on Jun. 19, 2014.

(51) Int. Cl.
*A61K 31/445* (2006.01)
*A61K 31/4468* (2006.01)
*A61K 31/593* (2006.01)
*A61B 5/055* (2006.01)

(52) U.S. Cl.
CPC .............. *A61K 31/445* (2013.01); *A61B 5/055* (2013.01); *A61K 31/4468* (2013.01); *A61K 31/593* (2013.01)

(58) Field of Classification Search
CPC .............. A61K 31/445; A61K 31/593; A61K 31/4468; A61B 5/055
USPC ................................................. 514/167, 327
See application file for complete search history.

(56) References Cited

U.S. PATENT DOCUMENTS

| | | | |
|---|---|---|---|
| 6,331,532 B1 | 12/2001 | Murphy et al. | |
| 7,442,711 B2 | 10/2008 | Matier et al. | |
| 7,691,896 B2 | 4/2010 | Myers et al. | |
| 7,754,463 B2 | 7/2010 | D'Andrea | |
| 7,838,023 B2 | 11/2010 | Garvey et al. | |
| 7,910,607 B2* | 3/2011 | Ba ........................ | C07D 211/94 514/316 |
| 7,923,037 B2 | 4/2011 | Tomaselli et al. | |
| 8,226,986 B2 | 7/2012 | Tomaselli et al. | |
| 2007/0123567 A1* | 5/2007 | Maxwell .............. | A61K 31/445 514/327 |
| 2007/0167419 A1* | 7/2007 | Lapchak .............. | A61K 31/573 514/171 |
| 2007/0275944 A1 | 11/2007 | Sharpe | |
| 2008/0200405 A1 | 8/2008 | Patil et al. | |
| 2010/0081689 A1 | 4/2010 | Wilcox et al. | |
| 2010/0240700 A1* | 9/2010 | Maxwell .............. | A61K 31/505 514/315 |
| 2010/0330599 A1 | 12/2010 | D'Andrea | |
| 2011/0130421 A1 | 6/2011 | Wilcox et al. | |
| 2011/0263504 A1 | 10/2011 | Cerami et al. | |
| 2012/0295937 A1 | 11/2012 | Linehan et al. | |

FOREIGN PATENT DOCUMENTS

| | | |
|---|---|---|
| WO | WO 9913875 | 3/1999 |
| WO | WO 9926582 | 6/1999 |
| WO | WO 9926954 | 6/1999 |
| WO | WO 0226231 | 4/2002 |
| WO | WO 03016323 | 2/2003 |
| WO | WO 03096991 | 11/2003 |
| WO | WO 2005019232 | 3/2005 |
| WO | WO 2005019233 | 3/2005 |
| WO | WO 2005051978 | 6/2005 |
| WO | WO 2005072295 | 8/2005 |
| WO | WO 2006113531 | 10/2006 |
| WO | 2013/020136 A2 | 2/2013 |

OTHER PUBLICATIONS

Chan et al., "Mutations in 2 distinct genetic pathways result in cerebral cavernous malformations in mice", May 2011, The Journal of Clinical Investigation, 121(5): 1871-1881.*
Dong et al., "Attenuation of Brain Damage and Cognitive Impairment by Direct Renin Inhibition in Mice With Chronic Cerebral Hypoperfusion", Oct. 2011, Hypertension, 58(4): 635-642.*
Rodrigues et al., "Cerebral microvascular inflammation in DOCA salt-induced hypertension: role of angiotensin II and mitochondrial superoxide", 2012, Journal of Cerebral Blood Flow & Metabolism, 32: 368-375.*
Gibson et al., "Strategy for Identifying Repurposed Drugs for the Treatment of Cerebral Cavernous Malformation", 2015, Circulation, 131: 289-299.*
Mitos Pharmaceuticals, "Efficacy Study of Tempol to Prevent Hair Loss From Radiotherapy to the Brain" NCT00801086, Dec. 1, 2008 3 pages (http://www.clinicaltrials.gov/ct2/show/NCT00801086).
National Institutes of Health Clinical Center (CC), "Topical MTS-01 for Dermatitis During Radiation and Chemotherapy for Anal Cancer" NCT01324141, Mar. 25, 2011, 4 pages. (http://www.clinicaltrials.gov/ct2/show/NCT01324141).
Amy Akers, PhD, "Cavernous Malformation," National Organization for Rare Disorders, years published 1989, 1995, 1998, 2003, 2010 and 2013 [online] https://rarediseases.org/rare-diseases/cavernous-malformation/.
Gibson, "Identification of Novel Treatments for a Hereditary Stroke Disorder Using Quantitative Phenotypic Fingerprinting," [online] The University of Utah. Retrieved from the Internet on Aug. 19, 2015: <URL: http://cdmbuntu.lib.utah.edu/utils/getfile/collection/etd3/id/3501/filename/3499.pdf>.

(Continued)

*Primary Examiner* — My-Chau T Tran
(74) *Attorney, Agent, or Firm* — Stoel Rives LLP

(57) ABSTRACT

Methods are provided of treating and preventing stroke diseases, such as cerebral cavernous malformation, by the administration of tempol and/or cholecalciferol.

20 Claims, 5 Drawing Sheets

(56) References Cited

OTHER PUBLICATIONS

United State Patent and Trademark Office, "International Search Report and Written Opinion," mailed Sep. 18, 2015 in International Patent Application No. PCT/US2015/036062.

Angioma Alliance 7th Annual Pathobiology of CCM Scientific Workshop, Chantilly, France Nov. 16-18, 2011 [online: http://www.angiomaalliance.org/documents/2011%20CCM%20Workshop%20Agenda.pdf].

* cited by examiner

METHODS OF TREATING AND PREVENTING VASCULAR INSTABILITY DISEASES

CROSS-REFERENCE TO RELATED APPLICATION

Under 35 U.S.C. §119(e), his application claims the benefit of U.S. Provisional Patent Application No. 62/014,540, filed Jun. 19, 2014, titled METHODS OF TREATING AND PREVENTING VASCULAR INSTABILITY DISEASES, the entire contents of which are hereby incorporated by reference herein.

STATEMENT REGARDING FEDERALLY SPONSORED RESEARCH OR DEVELOPMENT

This invention was made with government support under 5R01HL065648-09, 5R01CA163970-03, and 5R01NS080893-02 awarded by the National Institute of Health. The government has certain rights in the invention.

TECHNICAL FIELD

The present disclosure relates to methods of treating and/or preventing diseases. More particularly, the disclosure relates to methods of treating and/or preventing vascular instability diseases.

BACKGROUND

Cerebral cavernous malformation (CCM) is a stroke disorder comprising angiomas (i.e., vascular malformations) arising of the capillary vessels within the central nervous system (i.e., the brain, retina, or spine). CCM lesions may be leaky and unstable, with chronic and acute bleeding possibly leading to inflammation and stroke, respectively (see Gault J et al., Neurosurgery 55, 1-16 (2004)). CCM patients may also experience epilepsy and/or focal neurologic deficit (see Al-Shahi Salman R et al., Stroke 39, 3222-3230 (2008); and Josephson C B et al., Neurology 76, 1548-1554 (2011)). The primary treatment for CCM is neurosurgical resection (Batra S et al., Nat Rev Neurol 5, 659-670 (2009)). CCM generally occurs in two forms: sporadic and familial (or somatic and germline, respectively), which together may affect as many as 1 in 200 to 600 individuals in the United States (see Otten P G et al., Neurochirurgie 35, 82-83 (1989); Vernooij M W et al., N Engl J Med 357, 1821-1828 (2007); and Al Shahi Salman R et al., Lancet Neurol 11, 217-224 (2012)).

BRIEF DESCRIPTION OF THE DRAWINGS

The embodiments disclosed herein will become more fully apparent from the following description and appended claims, taken in conjunction with the accompanying drawings.

FIG. 2A depicts RHOA activation as described in Example 2.

FIG. 2B depicts pMLC activation as described in Example 2.

FIG. 3A depicts RAC1 activation as described in Example 2.

FIG. 3B depicts CDC-42 activation as described in Example 2.

DETAILED DESCRIPTION

Figure 1A:
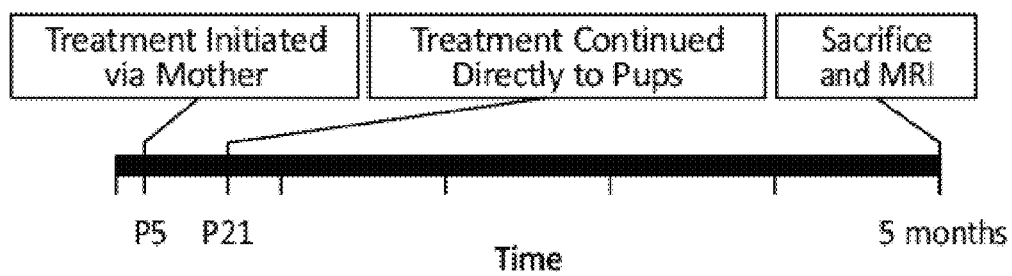
FIG. 1A depicts a timeline of the treatment and analysis as described in Example 1.

The present disclosure provides methods of treating vascular instability diseases including, but not limited to, stroke diseases such as cerebral cavernous malformation (CCM). This disclosure also provides methods of preventing vascular instability diseases including, but not limited to, CCM.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

A first aspect of the disclosure relates to methods of reducing a number of CCM lesions in a patient having at least one CCM lesion. Reduction in the growth rate and/or number of CCM lesions in the patient may decrease occurrence of CCM-associated signs or symptoms including, but not limited to, epilepsy, hemorrhage (e.g., intracerebral hemorrhage), and focal neurologic deficit.

In some embodiments, this disclosure provides methods of reducing a number of CCM lesions in a patient having at least one CCM lesion, wherein the methods comprise administering a therapeutically effective amount of tempol and/or a pharmaceutically acceptable salt thereof. The therapeutically effective amount of tempol(4-hydroxy-2,2,6,6-tetramethylpiperidin 1-oxyl) and/or the pharmaceutically acceptable salt thereof may also comprise a pharmaceutically acceptable carrier.

The methods disclosed herein may further comprise determining a number of CCM lesions in the patient. For example, the methods may comprise determining whether the patient has one CCM lesion, two CCM lesions, or more than two CCM lesions. The therapeutically effective amount of tempol and/or the pharmaceutically acceptable salt thereof, may at least partially depend on or be determined by the number of CCM lesions in the patient. For example, a patient having only one CCM lesion may require less, or a smaller dose of, tempol than a patient having two or more CCM lesions. In certain embodiments, magnetic resonance imaging (MRI) may be used to calculate or determine the number of CCM lesions in the patient. Other suitable methods of calculating or determining the number of CCM lesions in the patient may also be used.

The familial form of CCM accounts for approximately 20% of cases of CCM, and is generally associated with loss-of-function mutations in one of three genes: cerebral cavernous malformation 2 (CCM2); KRIT1, ankyrin repeat containing (KRIT1); and/or programmed cell death 10 (PDCD10) (see Riant F et al., FEBS J 277, 1070-1075 (2010). Individuals with multiple (i.e., two or more) CCM lesions and/or family history of CCM are generally considered to have the familial form of CCM and can have a higher risk of and/or higher frequency of CCM-associated signs or symptoms, such as hemorrhage (see Al-Shahi Salman R et al., Lancet Neurol 11, 217-224 (2012) and Flemming K D et al., Neurology 78, 632-636 (2012)). Without wishing to be bound by theory, the familial form of CCM may result from a heterozygous germline mutation in a gene selected from at least one of CCM2, KRIT1, and/or PDCD10. Individuals with a single CCM lesion and/or no family history of CCM are generally considered to have the sporadic form of CCM.

In some embodiments, the disclosed methods may further comprise identifying a patient having at least one CCM lesion, wherein the identification comprises identifying at least one mutation in at least one gene associated with CCM in the patient. For example, the at least one mutation may be identified in at least one gene selected from at least one of CCM2, KRIT1, and/or PDCD10. In certain embodiments, the at least one mutation may be identified in CCM2 or KRIT1.

In other embodiments, methods of reducing the number of CCM lesions in the patient may further comprise or alternatively comprise administering a therapeutically effective amount of cholecalciferol (vitamin D3), a derivative of cholecalciferol (including, but not limited to, calcidiol and calcitriol), and/or a pharmaceutically acceptable salt thereof. For example, the method of reducing the number of CCM lesions in the patient having at least one CCM lesion can comprise administering a therapeutically effective amount of: tempol and/or a pharmaceutically acceptable salt thereof; and a therapeutically effective amount of cholecalciferol, a derivative of cholecalciferol, and/or a pharmaceutically acceptable salt thereof.

In some embodiments, the patient may be a mammal. In certain embodiments, the patient may be a human. Any patient or subject having, or at risk of developing, CCM or at least one CCM lesion may potentially be a candidate for treatment with tempol, a pharmaceutically acceptable salt thereof, cholecalciferol, a derivative of cholecalciferol, and/or a pharmaceutically acceptable salt thereof.

Another aspect of the disclosure relates to methods of reducing a number of CCM lesions, or inhibiting development of one or more CCM lesions, in a patient at risk of developing at least one CCM lesion.

In some embodiments, this disclosure provides methods of reducing a number of CCM lesions, or inhibiting development of one or more CCM lesions, in a patient at risk of developing at least one CCM lesion, wherein the methods may comprise administering a therapeutically effective amount of tempol. In some other embodiments, methods of reducing the number of CCM lesions, or inhibiting development of one or more CCM lesions, in the patient at risk of developing at least one CCM lesion can comprise administering a therapeutically effective amount of tempol and/or a pharmaceutically acceptable salt thereof. The therapeutically effective amount of tempol and/or the pharmaceutically acceptable salt thereof may also comprise a pharmaceutically acceptable carrier.

In some embodiments, the methods may further comprise identifying a patient at risk of developing at least one CCM lesion, wherein the identification comprises identifying at least one mutation in at least one gene associated with CCM in the patient. For example, the at least one mutation can be identified in a gene selected from at least one of CCM2, KRIT1, and/or PDCD10. In certain embodiments, the at least one mutation may be identified in CCM2 or KRIT1. In some other embodiments, the methods of identifying the patient at risk of developing at least one CCM lesion may comprise identifying a heterozygous germline mutation in a gene selected from at least one of CCM2, KRIT1, and/or PDCD10. In yet other embodiments, the methods of identifying a patient at risk of developing at least one CCM lesion may comprise identifying a heterozygous germline mutation in CCM2.

In other embodiments, methods of reducing the number of CCM lesions, or preventing development of one or more CCM lesions, in the patient may further comprise or alternatively comprise administering a therapeutically effective amount of cholecalciferol, a derivative of cholecalciferol, and/or a pharmaceutically acceptable salt thereof. For example, the methods of reducing the number of CCM lesions, or preventing development of one or more CCM lesions, in the patient can comprise administering a therapeutically effective amount of: tempol and/or a pharmaceutically acceptable salt thereof; and a therapeutically effective amount of cholecalciferol, a derivative of cholecalciferol, and/or a pharmaceutically acceptable salt thereof. In some embodiments, the patient may be a mammal. In certain embodiments, the patient may be a human.

Another aspect of the disclosure relates to methods of inhibiting or preventing hemorrhage in a patient with at least one CCM lesion. Hemorrhage, or intracerebral hemorrhage, may be an effect (sign) or symptom of CCM. Up to 17% of CCM patients die due to intracerebral hemorrhages. Additionally, intracerebral hemorrhages may result in significant impacts on an individual's quality of life. Individuals with the highest risk of hemorrhage are generally those individuals with multiple CCM lesions and/or those individuals who have recently experienced a hemorrhage. For example, the rate of recurrent hemorrhage among CCM patients with a clinically symptomatic hemorrhage is 20% in the first year (see Flemming K D et al., Neurology 78, 632-636 (2012)). Further, it can be more difficult to treat patients having the familial form of CCM and/or having multiple CCM lesions via surgical resection. Thus, stabilization of CCM lesion number may prevent or reduce hemorrhage in CCM patients.

In some embodiments, a method of inhibiting or preventing hemorrhage in a patient with at least one CCM lesion may comprise administering a therapeutically effective amount of tempol and/or a pharmaceutically acceptable salt thereof. The therapeutically effective amount of tempol and/or the pharmaceutically acceptable salt thereof may also comprise a pharmaceutically acceptable carrier.

In other embodiments, the methods of inhibiting or preventing hemorrhage in the patient with at least one CCM lesion may further comprise identifying a patient with at least one CCM lesion who has experienced a hemorrhage within a predetermined time period prior to the administration of tempol and/or the pharmaceutically acceptable salt thereof. In certain embodiments, the predetermined time period may be one year. In certain other embodiments, the predetermined time period may be two years. Other predetermined time periods may also be used.

In some embodiments, the hemorrhage may be associated with, caused by, and/or a symptom of CCM. The hemorrhage can also have occurred in the cerebral vasculature of the patient.

In other embodiments, methods of inhibiting or preventing hemorrhage in the patient may further comprise or alternatively comprise administering a therapeutically effective amount of a compound selected from at least one of cholecalciferol, a derivative of cholecalciferol, and/or a pharmaceutically acceptable salt thereof. For example, the methods of inhibiting or preventing hemorrhage in the patient having at least one CCM lesion can comprise administering a therapeutically effective amount of: tempol and/or a pharmaceutically acceptable salt thereof; and a therapeutically effective amount of cholecalciferol, a derivative of cholecalciferol, and/or a pharmaceutically acceptable salt thereof. In some embodiments, the patient may be a mammal. In certain embodiments, the patient may be a human.

Another aspect of the disclosure relates to methods of reducing a permeability of cerebral vasculature in a patient having, or at risk of developing, CCM.

In some embodiments, this disclosure provides methods of reducing a permeability of cerebral vasculature in a patient having CCM, wherein the methods comprise administering a therapeutically effective amount of tempol. In some other embodiments, methods of reducing the permeability of the cerebral vasculature in the patient having CCM can comprise administering a therapeutically effective amount of tempol and/or a pharmaceutically acceptable salt thereof. The therapeutically effective amount of tempol and/or the pharmaceutically acceptable salt thereof may also comprise a pharmaceutically acceptable carrier.

In some embodiments, the disclosed methods may further comprise identifying a patient having CCM, wherein the identification comprises identifying at least one mutation in at least one gene associated with CCM in the patient. For example, at least one mutation can be identified in a gene selected from at least one of CCM2, KRIT1, and/or PDCD10. In certain embodiments, the at least one mutation may be identified in CCM2 or KRIT1.

In other embodiments, methods of reducing the permeability of the cerebral vasculature in the patient having CCM may further comprise or alternatively comprise administering a therapeutically effective amount of a compound selected from at least one of cholecalciferol, a derivative of cholecalciferol, and/or a pharmaceutically acceptable salt thereof. For example, the method of reducing the permeability of the cerebral vasculature in the patient having CCM can comprise administering a therapeutically effective amount of: tempol and/or a pharmaceutically acceptable salt thereof; and a therapeutically effective amount of cholecalciferol, a derivative of cholecalciferol, and/or a pharmaceutically acceptable salt thereof.

In some other embodiments, this disclosure provides methods of reducing the permeability of cerebral vasculature in a patient at risk of developing CCM, wherein the methods may comprise administering a therapeutically effective amount of tempol. In some other embodiments, methods of reducing the permeability of the cerebral vasculature of the patient at risk of developing CCM can comprise administering a therapeutically effective amount of tempol and/or a pharmaceutically acceptable salt thereof. The therapeutically effective amount of tempol and/or the pharmaceutically acceptable salt thereof may also comprise a pharmaceutically acceptable carrier.

In some embodiments, the methods of reducing the permeability of the cerebral vasculature may further comprise identifying a patient at risk of developing CCM, wherein the identification comprises identifying at least one mutation in at least one gene associated with CCM in the patient. For example, at least one mutation can be identified in a gene selected from at least one of CCM2, KRIT1, and/or PDCD10. In certain embodiments, the at least one mutation may be identified in CCM2 or KRIT1. In some other embodiments, the methods of identifying a patient at risk of developing CCM may comprise identifying a heterozygous germline mutation in a gene selected from at least one of CCM2, KRIT1, and/or PDCD10. In yet other embodiments, the methods of identifying the patient at risk of developing CCM may comprise identifying a heterozygous germline mutation in CCM2.

In other embodiments, methods of reducing the permeability of the cerebral vasculature in the patient at risk of developing CCM may further comprise or alternatively comprise administering a therapeutically effective amount of a compound selected from at least one of cholecalciferol, a derivative of cholecalciferol, and/or a pharmaceutically acceptable salt thereof. For example, the methods of reducing the permeability of the cerebral vasculature in the patient at risk of developing CCM can comprise administering a therapeutically effective amount of: tempol and/or a pharmaceutically acceptable salt thereof; and a therapeutically effective amount of cholecalciferol, a derivative of cholecalciferol, and/or a pharmaceutically acceptable salt thereof. In some embodiments, the patient may be a mammal. In certain embodiments, the patient may be a human.

Another aspect of the disclosure relates to methods of improving cerebrovascular health in a patient having CCM.

In some embodiments, this disclosure provides methods of improving cerebrovascular health in a patient having CCM, wherein the methods comprise administering a therapeutically effective amount of tempol. In some other embodiments, methods of improving cerebrovascular health in the patient having CCM can comprise administering a therapeutically effective amount of tempol and/or a pharmaceutically acceptable salt thereof. The therapeutically effective amount of tempol and/or the pharmaceutically acceptable salt thereof may also comprise a pharmaceutically acceptable carrier. In some embodiments, the disclosed methods may further comprise identifying a patient having CCM, as discussed above.

In other embodiments, methods of improving cerebrovascular health in the patient having CCM may further comprise or alternatively comprise administering a therapeutically effective amount of a compound selected from at least one of cholecalciferol, a derivative of cholecalciferol, and/or a pharmaceutically acceptable salt thereof. For example, the method of improving cerebrovascular health in the patient having CCM can comprise administering a therapeutically effective amount of: tempol and/or a pharmaceutically acceptable salt thereof; and a therapeutically effective amount of cholecalciferol, a derivative of cholecalciferol, and/or a pharmaceutically acceptable salt thereof.

Another aspect of the disclosure relates to methods of decreasing cerebrovascular inflammation in a patient having CCM.

In some embodiments, this disclosure provides methods of decreasing cerebrovascular inflammation in a patient having CCM, wherein the methods comprise administering a therapeutically effective amount of tempol. In some other embodiments, methods of decreasing cerebrovascular inflammation in the patient having CCM can comprise administering a therapeutically effective amount of tempol and/or a pharmaceutically acceptable salt thereof. The therapeutically effective amount of tempol and/or the pharmaceutically acceptable salt thereof may also comprise a pharmaceutically acceptable carrier. In some embodiments, the disclosed methods may further comprise identifying a patient having CCM, as discussed above.

In other embodiments, methods of decreasing cerebrovascular inflammation in the patient having CCM may further comprise or alternatively comprise administering a therapeutically effective amount of a compound selected from at least one of cholecalciferol, a derivative of cholecalciferol, and/or a pharmaceutically acceptable salt thereof. For example, the method of improving cerebrovascular health in the patient having CCM can comprise administering a therapeutically effective amount of: tempol and/or a pharmaceutically acceptable salt thereof; and a therapeutically effective amount of cholecalciferol, a derivative of cholecalciferol, and/or a pharmaceutically acceptable salt thereof.

In some embodiments, this disclosure provides methods of treating or preventing Hereditary Hemorrhagic Telangiectasia (HHT), wherein the methods may comprise administering a therapeutically effective amount of tempol, and/or a pharmaceutically-acceptable salt thereof.

In other embodiments, the methods of any of the foregoing embodiments may further comprise or alternatively comprise administering a therapeutically effective amount of a compound selected from at least one of: tempo (2,2,6,6-Tetramethyl-piperidin-1-yl)oxyl), 4-Amino-tempo (4-Amino-(2,2,6,6-Tetramethyl-piperidin-1-yl)oxyl), $CuSO_4$, $MnCl_2$, Tiron (4,5-dihydroxy-1,3-benzene disulfonic acid), PEG-SOD (polyethylene glycol superoxide dismutase), aloin ((10S)-10-Glucopyranosyl-1,8-dihydroxy-3-(hydroxymethyl)-9(10H)-anthracenone), apomorphine hydrochloride, dimercaprol, gedunin, and pindolol; a derivative thereof; and/or a pharmaceutically acceptable salt thereof.

EXAMPLES

To further illustrate these embodiments, the following examples are provided. These examples are not intended to limit the scope of the claimed invention, which should be determined solely on the basis of the attached claims.

Example 1

Chronic Tempol and Cholecalciferol Treatment in Ccm2 ecKO Mice

Chronic treatment studies of the effects of tempol and cholecalciferol in inducible endothelial-specific Ccm2 knockout mice ($Ccm2^{f/-}$; $+/Tg(Pdgfb-iCreER^{T2})$), also referred to herein as Ccm2 ecKO mice or endothelial knockout mice, were performed, inter alia, to evaluate the potential of tempol and/or cholecalciferol administration for the treatment of CCM disease (see Chan A C et al., J Clin Invest 121, 1871-1881 (2011) regarding the Ccm2 ecKO mice). 5 days after birth (P5), Ccm2 ecKO mice litters were assigned to a standard chow (HARLAN 2018, 1.5 IU/g D3), a standard chow plus tempol in drinking water (1 mM), or a cholecalciferol-enhanced chow (HARLAN 2018+25 IU/g D3). The chow was provided to the mother of each litter until the mice were weaned at P21. Mice from each litter continued on their respective diets until 5 months of age, a point at which 100% of untreated endothelial-specific Ccm2 knockout mice have cerebrovascular lesions detectable by MRI. FIG. 1A illustrates a timeline of the treatment and analysis of tempol or cholecalciferol in Ccm2 ecKO mice as described herein.

At 5 months of age, mice were sacrificed by exsanguination (blood was collected for later analysis), and subsequent perfusion with saline and then 4% formaldehyde. Brains were dissected from the skull, and postmortem MRI scanning was performed. A gradient recalled echo sequence was used to acquire coronal slices spanning the whole brain. Sequence parameters were as follows: repetition time, 328 ms; echo time, 5.4 ms; flip-angle, 40°; 12 averages, in-plane-resolution, 125 µm×125 µm; and slice thickness, 0.5 mm. For a representative subset of brains (for use in 3D reconstructions), high-resolution 3D gradient echo was acquired using the following parameters: isotropic voxel size of 78 µm×78 µm×78 µm over 9 hours. Other sequence parameters were as follows: repetition time, 250 ms; echo time, 7.5 ms; flip angle, 30°; and 2 averages. Lesion area and number were quantified by two blinded reviewers using IMAGEJ and OSIRIX software. Specifically, each reviewer was provided with all MRIs which had been relabeled randomly. Each reviewer then used software to circle all 'lesions' of any size in every slice of every MRI from all mice. Contiguous lesions were outlined as one large lesion.

Figure 1B:
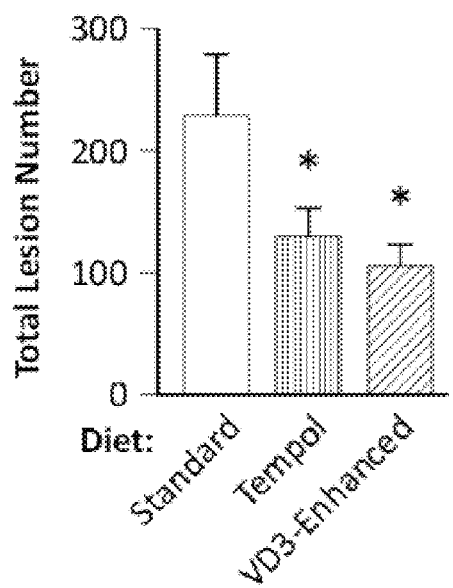
FIG. 1B is a graph depicting numbers of cerebral cavernous malformation (CCM) lesions as described in Example 1.
Figure 1C:
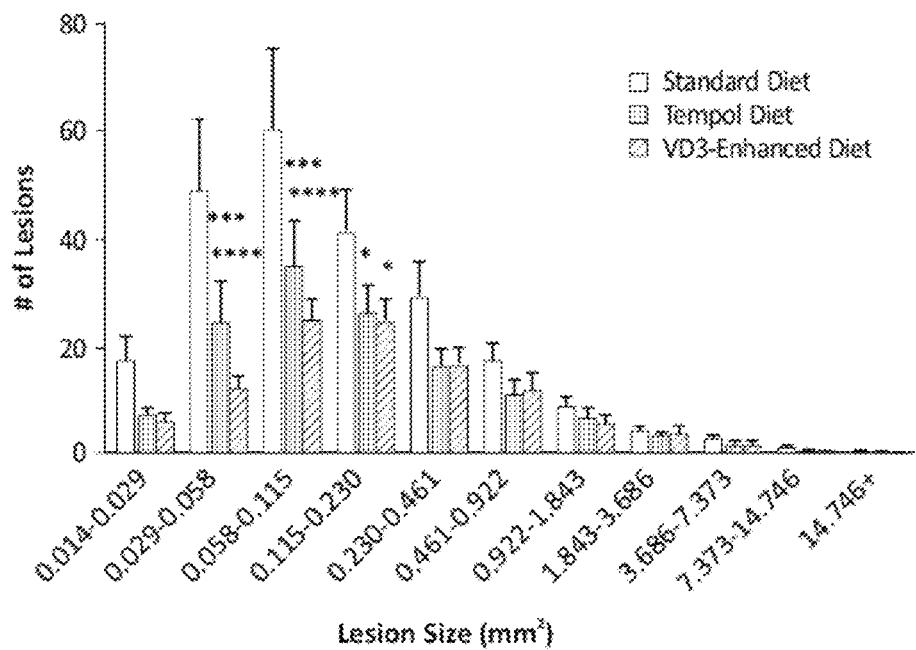
FIG. 1C is a graph depicting numbers and sizes of CCM lesions as described in Example 1.
Figure 1D:
FIG. 1D depicts reconstructions of murine brains and CCM lesions as described in Example 1.

The results of both reviewers were tabulated. 3 D reconstructions were assembled using OSIRIX software by a blinded reviewer. Mice receiving the diet enriched with tempol or cholecalciferol had approximately half as many lesions compared to those receiving the standard chow. FIG. 1B depicts a normalized number of CCM lesions as measured by MRI in Ccm2 ecKO mice. The term "VD3-Enhanced" as used herein, and specifically in FIGS. 1B and 1C, refers to a vitamin D3-enhanced or a cholecalciferol-enhanced diet. When lesion numbers were compared based on cross section area as quantified on MRI, both treatments appeared to significantly reduce lesions across the most common lesion sizes, and there was a strong trend toward reduction of all lesion sizes. FIG. 1C is a graph depicting the number of lesions of various sizes as measured by MRI in Ccm2 ecKO mice. The effect of tempol and cholecalciferol supplementation was qualitatively apparent when comparing MRI-based three-dimensional reconstructions of mouse brains. FIG. 1D illustrates three-dimensional reconstructions of the brain (grey/cream) and lesions (red) for representative brains from each of the above-described treatment arms, wherein the mouse brain with the median number of lesions from each treatment group is shown (the upper-most brain is for the control group; the middle-most brain is for the cholecalciferol group; and the bottom-most brain is for the tempol group). The graphs of FIGS. 1B and 1C depict±standard error of the mean (SEM). * denotes $P<0.05$,  denotes $P<0.01$, * denotes $P<0.001$, and **** denotes $P<0.0001$.

Example 2

Analysis of the Timing of Cholecalciferol Effects on the Endothelium

The timing of effects of cholecalciferol on the endothelium was assessed by evaluating the effect of knockdown of CCM2, and subsequent treatment with cholecalciferol, on a panel of signaling pathways associated with endothelial instability. The signaling pathways assessed included: ADP-ribosylation factor 6 (ARF6), cell division control protein 42 homolog (CDC42), transforming protein RhoA (RHOA), phosphorylation of myosin light chain (pMLC), Ras-related C3 botulinum toxin substrate 1 (RAC1), and Ras-related protein R-Ras (RRAS) (see Broman M T et al., Circ Res 98, 73-80 (2006); Broman M T et al., Trends Cardiovasc Med 17, 151-156 (2007); Eliceiri B P et al., Mol Cell 4, 915-924 (1999); Sawada J et al., Cancer Cell 22, 235-249 (2012); Weis S et al., J Cell Biol 167, 223-229 (2004); Wojciak-Stothard B et al., Vascul Pharmacol 39, 187-199 (2002); and Zhu W et al., Nature 492, 252-255 (2012)).

Wild-type, siCTRL, or siCCM2 treated HMVEC-D cells were incubated with either 100 nM or 10 µM cholecalciferol (TOCRIS BIOSCIENCE), 7-DHC (SIGMA-ALDRICH), or vehicle (0.5% DMSO) for 60 minutes (pMLC, ARF6, RAC, CDC42, RRAS) or 24 hours (RHOA), unless otherwise indicated. After treatment, the cells were washed with ice-cold PBS and lysed in 50 mM Tris pH 7.4, 150 mM NaCl, 10 mM $MgCl_2$, 10% glycerol, 1% NP-40, 1× protease inhibitors, and 1× phosphatase inhibitors.

For RhoA, ARF6, Rac1/cdc42, and R-Ras activation assays, crude total cell lysate were generated and GTP-RhoA, ARF6, Rac1/cdc42, and R-Ras were precipitated with Rhotekin-RBD (EMD MILLIPORE), GGA3-PBD (CELL BIOLABS), PAK-1-PBD (EMD MILLIPORE), and Raf-1 RBD, respectively. Following three washes with lysis buffer, bound proteins were eluted with 2× sample buffer. RhoA, ARF6, Rac1/cdc42, and R-Ras were detected by western blotting with antibodies (RhoA, Rac1, and R-Ras antibodies were from CELL SIGNALING TECHNOLOGY; ARF6 and cad42 antibodies were from EMD MILLIPORE).

Figure 2C:
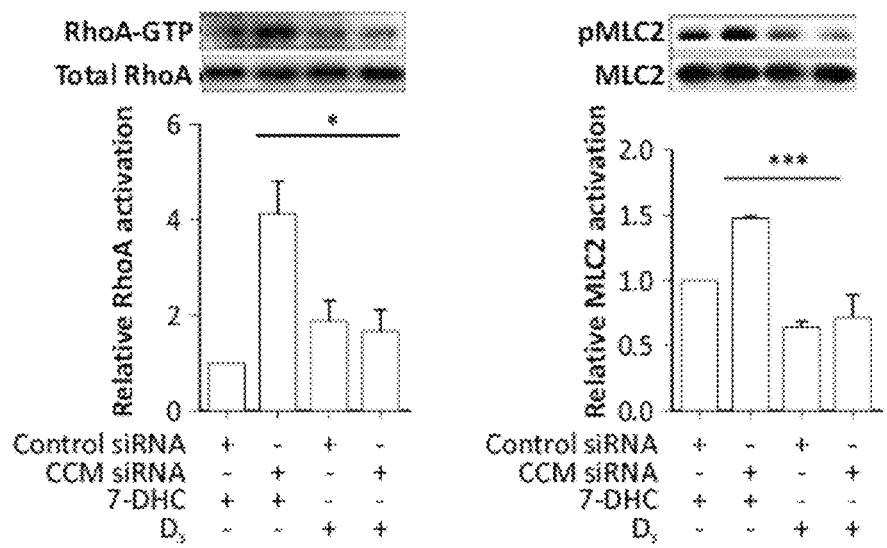
FIG. 2C depicts ARF6 activation as described in Example 2.
Figure 2C:
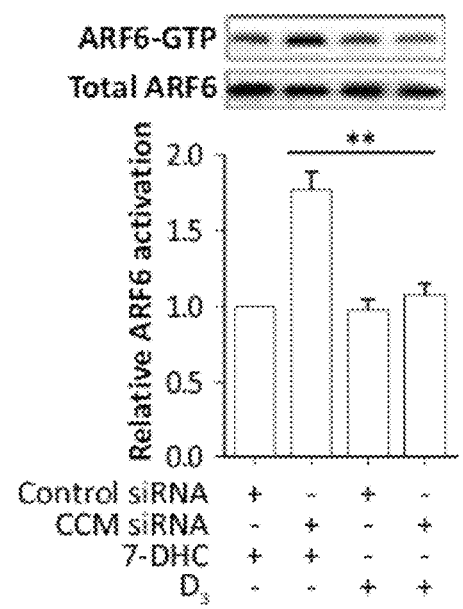
Figure 3C:
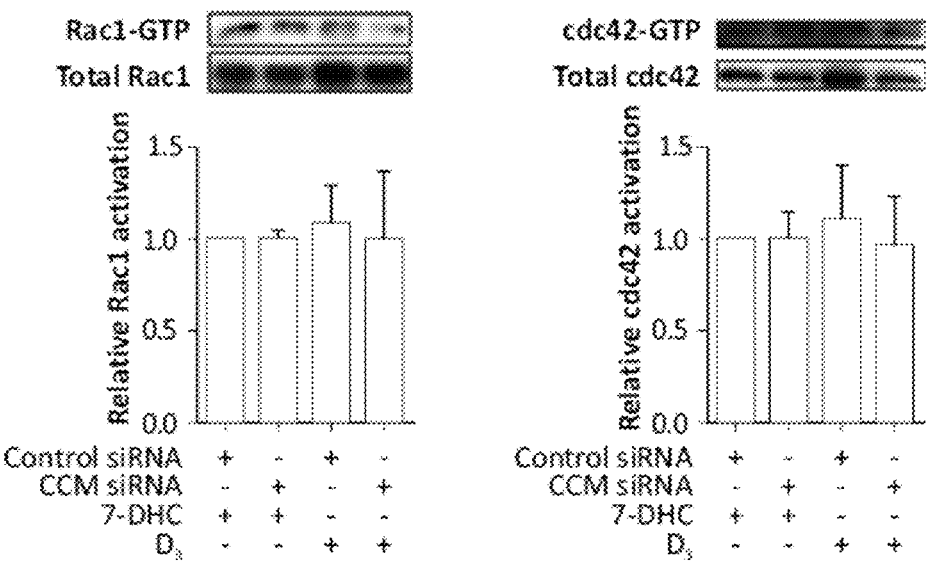
FIG. 3C depicts R-RAS activation as described in Example 2.
Figure 3C:
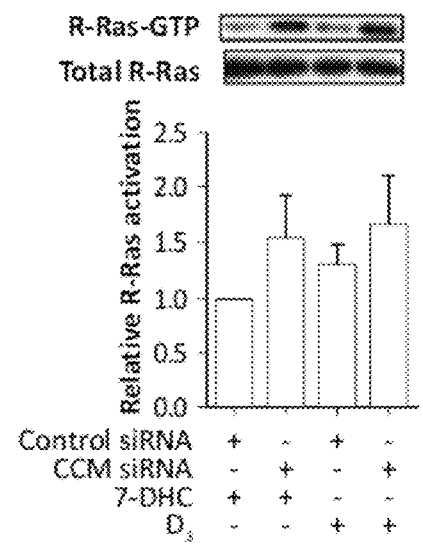
Figure 4A:
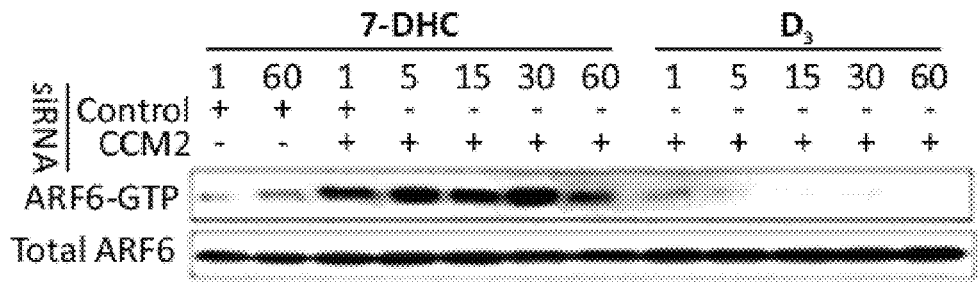
FIG. 4A depicts cholecalciferol rescue of CCM2-induced activation of ARF6 as described in Example 2.
Figure 4B:
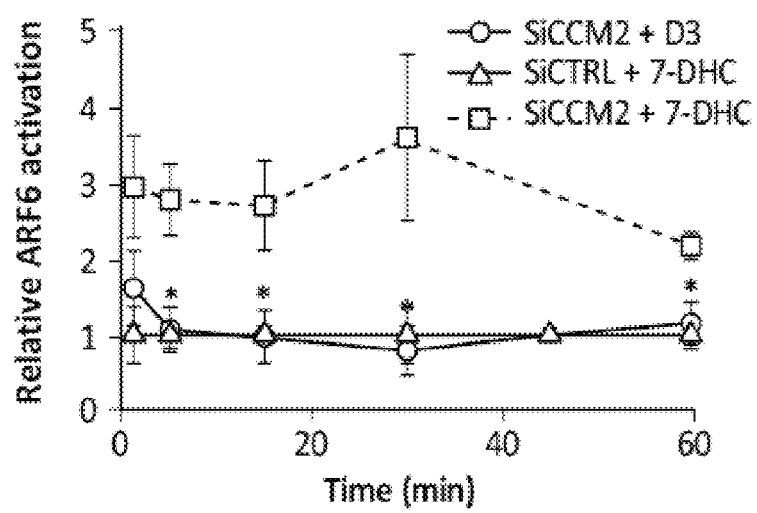
FIG. 4B is a graph depicting a quantification of the results of FIG. 4A.

Treatment of monolayers with cholecalciferol inhibited the CCM2 knockdown-induced activation of ARF6, RHOA, and pMLC (see FIGS. 2A-2C). Knockdown of CCM2 did not appear to affect activation of CDC42, RAC1, or RRAS; nor did treatment of up to 10 µM cholecalciferol appear to basally inhibit activation of these markers (see FIGS. 3A-3C). Due to a strong role for ARF6 as a central modulator of endothelial permeability, the timing of the effects of cholecalciferol on ARF6 activation were further examined, and inhibition of ARF6 activation was found to occur within 5 minutes (see FIGS. 4A and 4B). FIGS. 2A-2C, 4A, and 4B depict mean±SEM for three or more independent experiments. * denotes $P<0.05$,  denotes $P<0.01$, and * denotes $P<0.001$. With reference to FIGS. 3A-3C, all bars represent mean±SEM.

Taken together, the data, as described above, suggest that cholecalciferol, even at physiologic doses, can rapidly and directly inhibit multiple key intracellular signaling pathways that play a role in endothelial activation and stability in the context of mutation-induced destabilization.

It will be apparent to those having skill in the art that many changes may be made to the details of the above-described embodiments without departing from the underlying principles of the invention.

The invention claimed is:

1. A method of reducing a growth rate of a number of cerebral cavernous malformation (CCM) lesions in a patient having, or at risk of developing, at least one CCM lesion, the method comprising administering a therapeutically effective amount of tempol, a derivative thereof, or a pharmaceutically-acceptable salt of the foregoing.

2. The method of claim 1, further comprising determining a number, a size, or both, of at least one CCM lesion.

3. The method of claim 2, further comprising determining the number and the size of at least one CCM lesion prior to administration.

4. The method of claim 3, further comprising determining the number and the size of at least one CCM lesion after administration.

5. The method of claim 1, wherein the derivative of tempol comprises tempo, 4-amino tempo, or a pharmaceutically-acceptable salt thereof.

6. The method of claim 1, further comprising identifying a patient having at least one CCM lesion.

7. The method of claim 1, further comprising administering a therapeutically effective amount of cholecalciferol, a derivative thereof, or a pharmaceutically acceptable salt of any of the foregoing.

8. A method of treating a sign or symptom of cerebral cavernous malformation (CCM) lesions in a patient having at least one CCM lesion, comprising administering a therapeutically effective amount of tempol, a derivative thereof, or a pharmaceutically acceptable salt thereof to the patient.

9. The method of claim 8, wherein the sign or symptom of CCM is selected from at least one of a presence of the at least one CCM lesion, intracerebral hemorrhage, increased permeability of cerebral vasculature, epilepsy, or focal neurological deficit.

10. The method of claim 9, further comprising identifying a patient having at least one CCM lesion who has experienced an intracerebral hemorrhage within a predetermined time period prior to the administration of tempol or a pharmaceutically-acceptable salt thereof.

11. The method of claim 10, wherein the predetermined time period is one year.

12. The method of claim 8, further comprising identifying a patient having at least one CCM lesion and determining a number, a size, or both, of the at least one CCM lesion.

13. The method of claim 12, wherein identifying the patient having at least one CCM lesion comprises identifying a mutation in at least one gene associated with CCM in the patient.

14. The method of claim 13, wherein the at least one gene associated with CCM is selected from at least one of CCM2, KRIT1, or PDCD10.

15. The method of claim 8, further comprising determining a number of CCM lesions using magnetic resonance imaging.

16. The method of claim 8, further comprising administering a therapeutically effective amount of cholecalciferol, a derivative thereof, or a pharmaceutically acceptable salt of any of the foregoing.

17. A method of decreasing cerebrovascular inflammation, reducing cerebrovascular permeability, or both, in a patient having at least one cerebral cavernous malformation (CCM) lesion, comprising administering a therapeutically effective amount of tempol, a derivative thereof, or a pharmaceutically acceptable salt thereof to the patient.

18. The method of claim 17, further comprising identifying a patient having at least one CCM lesion and determining a number, a size, or both, of the at least one CCM lesion.

19. The method of claim 18, wherein identifying the patient having at least one CCM lesion comprises identifying a mutation in at least one gene associated with CCM in the patient.

20. The method of claim 17, further comprising administering a therapeutically effective amount of cholecalciferol, a derivative thereof, or a pharmaceutically acceptable salt of any of the foregoing.

* * * * *